(12) United States Patent
Doerr

(10) Patent No.: US 10,661,087 B2
(45) Date of Patent: May 26, 2020

(54) ELECTRICAL IMPLANT OR IMPLANT SYSTEM

(71) Applicant: BIOTRONIK SE & CO. KG, Berlin (DE)

(72) Inventor: Thomas Doerr, Berlin (DE)

(73) Assignee: Biotronik Se & Co. KG, Berlin (DE)

(*) Notice: Subject to any disclaimer, the term of this patent is extended or adjusted under 35 U.S.C. 154(b) by 292 days.

(21) Appl. No.: 15/725,314

(22) Filed: Oct. 5, 2017

(65) Prior Publication Data

US 2018/0104501 A1  Apr. 19, 2018

(30) Foreign Application Priority Data

Oct. 14, 2016 (EP) ..................................... 16193885

(51) Int. Cl.
| | | |
|---|---|---|
| *A61N 1/375* | (2006.01) | |
| *A61N 1/378* | (2006.01) | |
| *A61N 1/05* | (2006.01) | |
| *A61B 5/00* | (2006.01) | |
| *A61N 1/362* | (2006.01) | |

(52) U.S. Cl.
CPC ........ *A61N 1/37518* (2017.08); *A61B 5/6861* (2013.01); *A61N 1/05* (2013.01); *A61N 1/057* (2013.01); *A61N 1/362* (2013.01); *A61N 1/378* (2013.01); *A61N 1/3756* (2013.01); *A61N 1/3758* (2013.01); *A61N 1/37512* (2017.08); *A61N 2001/0578* (2013.01)

(58) Field of Classification Search
CPC ..................................................... A61N 1/362
See application file for complete search history.

(56) References Cited

U.S. PATENT DOCUMENTS

| | | | | |
|---|---|---|---|---|
| 4,827,940 A | * | 5/1989 | Mayer .................... | A61B 5/042 600/375 |
| 5,383,924 A | * | 1/1995 | Brehier .................. | A61N 1/057 607/126 |
| 6,419,674 B1 | * | 7/2002 | Bowser .................. | A61N 1/057 606/45 |
| 7,715,174 B1 | | 5/2010 | Beauvais et al. | |
| 2004/0186576 A1 | | 9/2004 | Biscup et al. | |
| 2008/0188902 A1 | | 8/2008 | Starke | |
| 2008/0288030 A1 | | 11/2008 | Zhang et al. | |

(Continued)

*Primary Examiner* — Carl H Layno
*Assistant Examiner* — Jennifer L Ghand
(74) *Attorney, Agent, or Firm* — Laurence A. Greenberg; Werner H. Stemer; Ralph E. Locher

(57) ABSTRACT

An electrical implant or implant system includes an energy supply unit or is connected to an energy supply unit and includes at least one fixing device for permanently fixing the electrical implant or implant system to bodily tissue, or is connected to the fixing device. At least two implant components are releasably mechanically connected to one another. A first of the implant components includes at least parts of the fixing device. A second of the implant components includes an electromechanical component which, as a result of current drain or current feed, can swell in such a way that it causes a swelling at an outer contour of the electromechanical component at least at one point. The electromechanical component is disposed in such a way that a swelling of the electromechanical component results in a separation of the mechanical connection between the first and second implant components.

14 Claims, 3 Drawing Sheets

(56) References Cited

U.S. PATENT DOCUMENTS

2013/0253347 A1 9/2013 Griswold et al.
2014/0379048 A1 12/2014 Von Arx et al.
2016/0051824 A1 2/2016 Doerr et al.

* cited by examiner

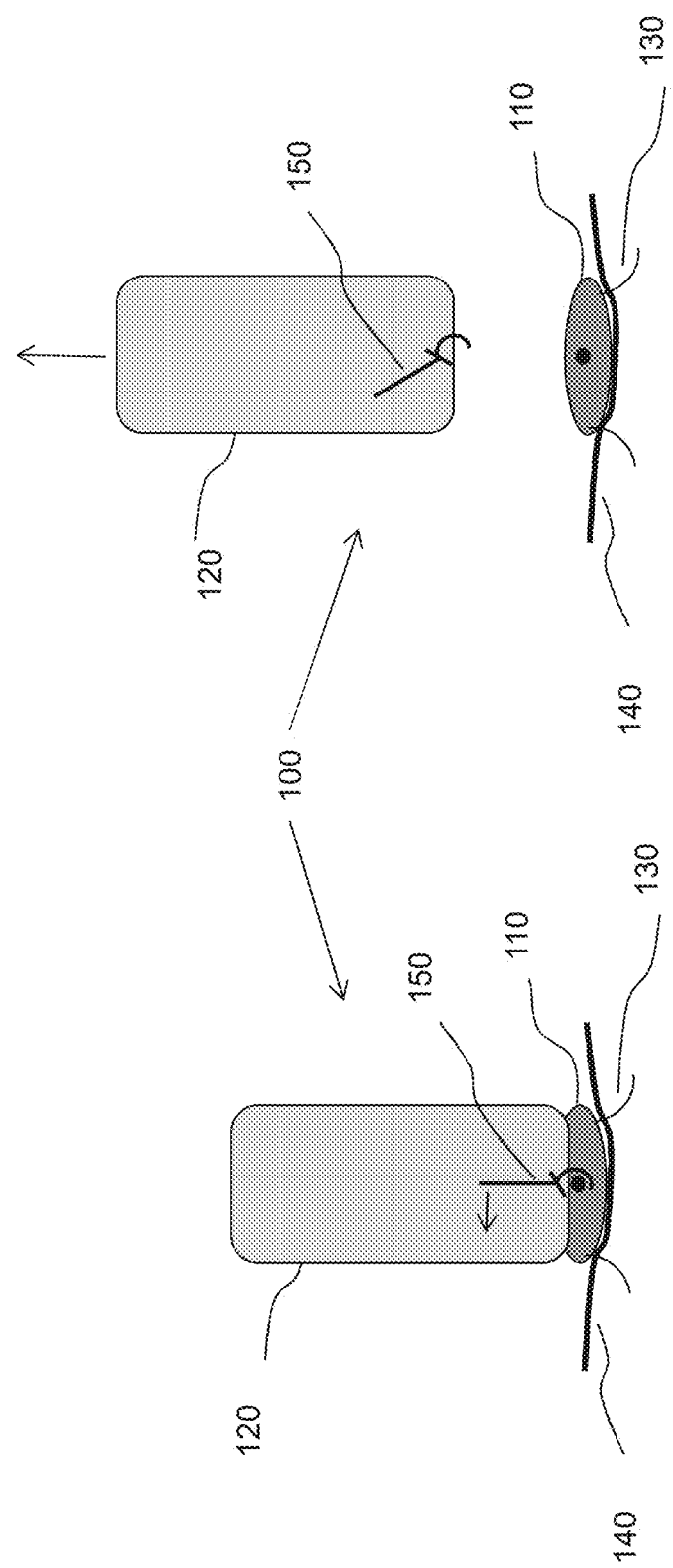

ELECTRICAL IMPLANT OR IMPLANT SYSTEM

CROSS-REFERENCE TO RELATED APPLICATION

This application claims the benefit, under 35 U.S.C. § 119, of European Patent Application EP 16193885.7, filed Oct. 14, 2016; the prior application is herewith incorporated by reference in its entirety.

BACKGROUND OF THE INVENTION

Field of the Invention

The invention relates to an electrical implant or implant system, which includes an energy supply unit or is connected to an energy supply unit and which includes at least one fixing device for permanently fixing the electrical implant or implant system to bodily tissue, or is connected to such a fixing device.

Electrical implants or implant systems of that type by way of example can be cardiac pacemakers fully implantable in a chamber of the heart (ventricle), wherein the stimulation electrode poles are disposed directly on the housing of the cardiac pacemaker, so that no electrode leads are necessary. Cardiac pacemakers of that type are known as implantable leadless pacemakers (ILPs). In order to ensure a reliable stimulation of the respective chambers of the heart by the ILP, it is necessary to fix a heart stimulator of that type as an active electrical implant in the chamber of the heart in question. By way of example, a fixing device of the electrical implant can be anchored in the trabecular structure of the ventricle, with the result that the implant can only be explanted with great difficulty, or even cannot be explanted at all.

SUMMARY OF THE INVENTION

It is accordingly an object of the invention to provide an electrical implant or implant system which makes a contribution to solving this problem.

With the objects of the invention in view there is provided an active electrical implant or implant system of the type mentioned at the outset, which has at least two implant components releasably mechanically connected to one another, of which a first of the implant components includes at least parts of the fixing device. A second of the implant components includes an electromechanical component, which, as a result of a current drain or a current feed, can swell in such a way that it causes a swelling at the outer contour of the electromechanical component at least at one point. The electromechanical component is disposed in such a way that a swelling of the electromechanical component results in a separation of the mechanical connection between the first and second implant components.

This results in the advantage that at least the second implant component can be relatively easily explanted following a separation from the first implant component, whereas the first implant component can remain at the site of implantation as appropriate. A further advantage is that the separation of the first implant component from the second implant component can be electrically controlled. A separation of this type for example can therefore also be triggered remotely by transmitting corresponding control signals to the active electrical implant or implant system.

The electromechanical component preferably has an electrical energy storage device which in turn for example includes a battery and/or a capacitor. Batteries often have the property of swelling when they are deeply discharged, and therefore the electromechanical component can be constructed so that a deep-discharge of the battery results in a swelling at the outer contour of the electromechanical component. Capacitors on the other hand can swell if they are charged beyond a known maximum voltage. Accordingly, the capacitor of the electromechanical component can also be disposed so that a swelling at the outer contour of the electromechanical component results. In fact, the electromechanical component can even be constituted by an individual battery or an individual capacitor.

If the electromechanical component includes a battery, it is preferable if the active electrical implant or implant system is configured to deeply discharge the battery in order to trigger the swelling of the electromechanical component.

If the electromechanical component is a capacitor or includes a capacitor, the active electrical implant or implant system is preferably configured to charge the capacitor beyond the nominal voltage of the capacitor in order to trigger the swelling of the electromechanical component.

If the electromechanical component is an electrolytic capacitor or includes an electrolytic capacitor, the active electrical implant or implant system is preferably adapted to charge the electrolytic capacitor against its polarity in order to trigger the swelling of the electromechanical component.

The electromechanical component is preferably an encapsulated part, which, when a voltage is applied or a current is injected, causes a swelling due to the fact that gas forms as a result of electrolysis in the encapsulated part.

It is also preferred if the electrical implant or implant system has a telemetry unit and is adapted to trigger a swelling of the electromechanical component following receipt of a corresponding telemetry signal.

It is particularly preferred if the electromechanical component is part of the energy supply unit of the electrical implant or implant system and includes a battery, wherein the electromechanical component is dimensioned in such a way that, when the battery of the energy supply unit is fully depleted, this results in a separation of the mechanical connection between the first and the second implant components. This embodiment has the advantage that the first and the second implant components automatically separate from one another when the battery of the energy supply unit is depleted and consequently swells.

The battery of the energy supply unit is therefore preferably disposed and dimensioned in such a way that, when the battery is fully depleted, it swells to such an extent that it causes a separation of the mechanical connection between the first and the second implant components.

In an advantageous embodiment the mechanical connection between the first and the second implant components is a detent connection, and the outer contour of the electromechanical component swelling as a result of a current drain or a current feed is adjacent the outer contour of the first implant component, in the state in which the two implant components are latched to one another, in such a way that a swelling of the outer contour causes such a force between the outer contour of the first implant component and the outer contour of the second implant component that the detent connection releases.

The active electrical implant or implant system is preferably an implantable cardiac pacemaker without electrode leads, i.e. an implantable leadless pacemaker (ILP). It is also advantageous if the active electrical implant or implant system is an implantable sensor.

In a further advantageous embodiment the electrical implant or implant system is a sensor lead or electrode lead.

The first implant component intended for fixing or anchoring at the site of implantation may be provided with tissue anchors as the fixing device.

Other features which are considered as characteristic for the invention are set forth in the appended claims.

Although the invention is illustrated and described herein as embodied in an electrical implant or implant system, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1A shows a schematic depiction of an implant with two implant components in the mechanically connected state thereof, FIG. 1B shows the implant from FIG. 1A with implant components mechanically released from one another.

DETAILED DESCRIPTION OF THE INVENTION

Figures 2A, 2B:
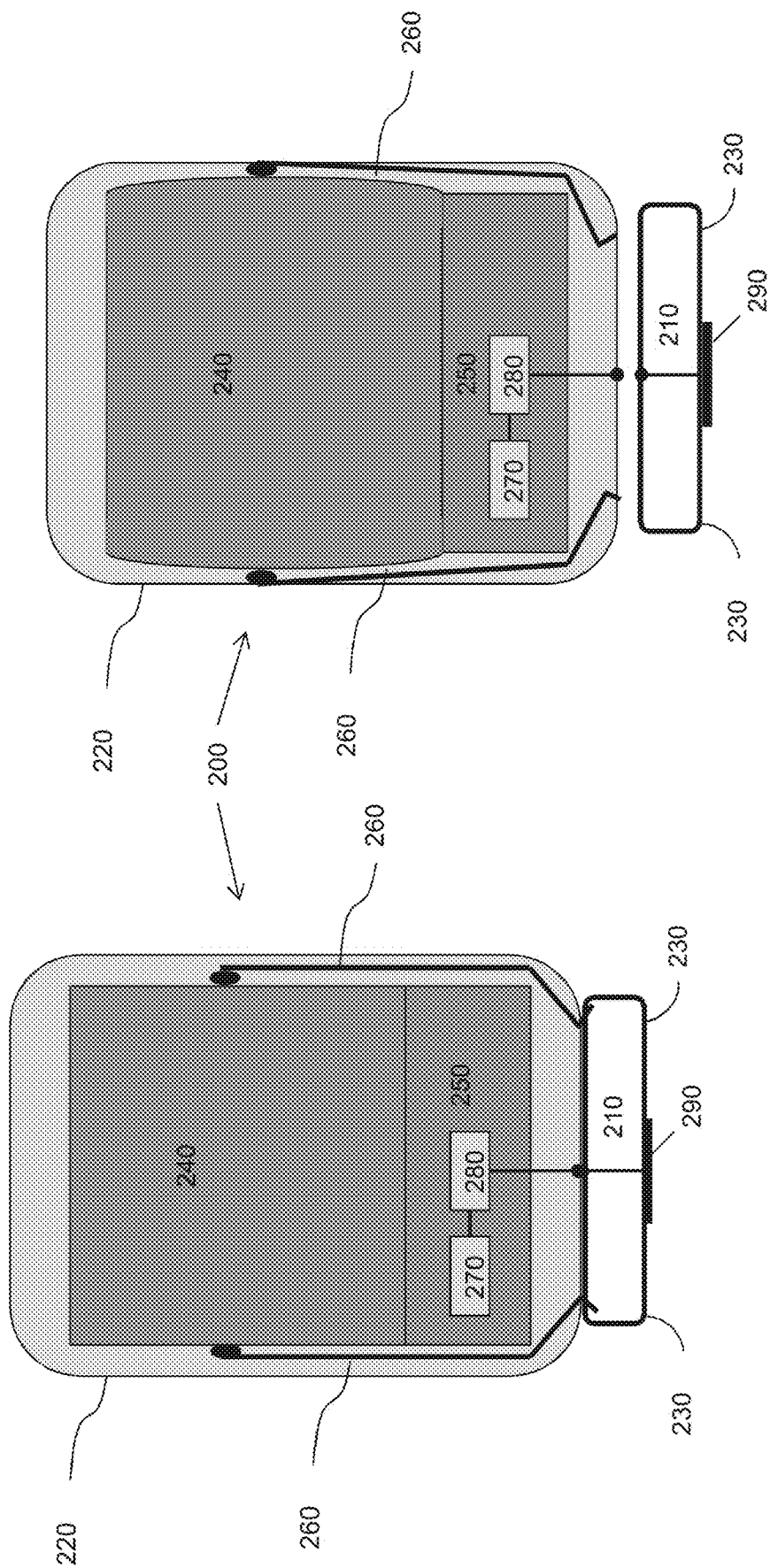
FIG. 2A shows a schematic depiction of an implant with two implant components mechanically connected to one another inclusive of a depiction of some sub-components of the second implant component.
FIG. 2B shows the implant from FIG. 2A with implant components mechanically separated from one another.

Referring now to the figures of the drawing in detail and first, particularly to FIGS. 1A and 1B thereof, there is seen an implantable leadless cardiac pacemaker 100 as an example of an active electrical implant or implant system. The concept underlying this invention, however, can be applied in other implants or implant systems, including implant systems that include electrode leads.

The cardiac pacemaker 100 shown in FIGS. 1A and 1B is partly explantable and has a first implant part 110, which as a first implant component includes a fixing device in the form of nitinol anchors 130. A second, active implant part 120 is releasably mechanically connected to the first implant part 110 and usually includes a battery and a control electronics unit (not illustrated in FIGS. 1A and 1B). The nitinol anchors 130 of the first implant part 110 serve as a fixing device for anchoring the implant 100 for example to heart tissue. Following the implantation of the implant 100, the nitinol anchors 130 become firmly embedded in the myocardial tissue 140. Such anchors typically grow into the tissue in such a way that after a few weeks they can only be removed surgically. The first implant part 110 is therefore practically impossible to remove from the tissue.

The mechanical connection 150 between the first implant part 110 and the second, active implant part 120 is therefore constructed releasably and in the form of a locking device. This makes it possible to explant the second, active implant part following release of the locking device 150, for example if the battery thereof is depleted. The locking device 150 can be released here by a corresponding programming of the implant 100. The second, active implant part 120 can then be explanted, whereas the first implant part 110 can remain in the heart together with the fixing device and in particular the anchors 130.

FIGS. 2A and 2B shows a variant of the implant 200 in the form of a cardiac pacemaker in a slightly more detailed depiction. Again, it can be seen that the implant 200 is assembled from a first implant part 210 and a second, active implant part 220. The first implant part 210 again includes a fixing device, which inter alia includes anchors 230 made for example from nitinol, which can become embedded in the myocardium after implantation. In addition, a stimulation electrode 290 is disposed on the first implant part 210 and after implantation is in electrical contact with the myocardium.

The second, active implant component 220 contains an energy source in the form of a battery 240 and a control and therapy electronics unit 250 electrically connected to the battery. The electronics unit includes inter alia a telemetry unit 270 and a stimulation unit 280.

The first implant part 210 and the second implant part 220 are mechanically connected to one another in the depicted exemplary embodiment by two locking levers 260. The locking levers 260 are disposed so that they release the locking between the first implant part 210 and the second implant part 220 when the battery 240 swells and a swelling outer contour of the battery 240 presses against corresponding arms of the locking levers 260.

The battery 240 swells for example when it is fully discharged when it reaches its end of service (EOS). The end of service of the battery 240 in this way leads automatically to a release of the mechanical connection between the first implant part 210 and the second implant part 220.

Alternatively or additionally, the control and therapy electronics unit 250 can also be constructed so that it triggers a discharge of the battery 240 and therefore swelling thereof in the event of a corresponding telemetry signal, with the result that the mechanical connection between the first implant component 210 and the second implant component 220 is separated. The control and therapy electronics unit 250 includes the telemetry unit 270 for this purpose.

The battery 240 is thus formed as an electromechanical component, which is constructed so that it swells at specific points of its outer contour when it is fully discharged. Alternative electromechanical components can for example contain capacitors, additionally or alternatively to the battery.

As can also be inferred from FIGS. 2A and 2B, the first implant component 210, anchored in the myocardium, includes a stimulation electrode 270, which in the mechanically connected state of the two implant components 210 and 220 is electrically connected to the stimulation unit 280. This electrical connection between the stimulation electrode 290 and the stimulation unit 280 also releases after the mechanical separation of the first implant component 210 from the second implant component 220. It should be noted that the electrode 290 can also be a sensing electrode and accordingly a corresponding sensing unit can also be provided instead of the stimulation unit 280. Combinations of these units can be provided. In addition, the implant 200 can also include further stimulation or sensing electrodes.

Figure 3B:
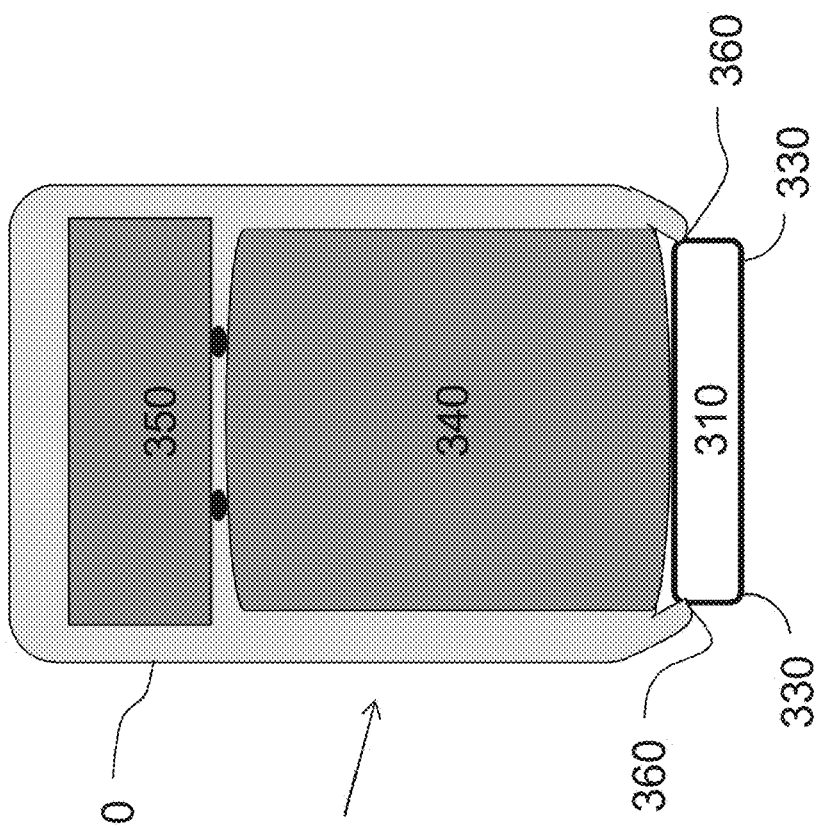
FIG. 3B shows the implant from FIG. 3A with implant components mechanically separated from one another.
Figure 3A:
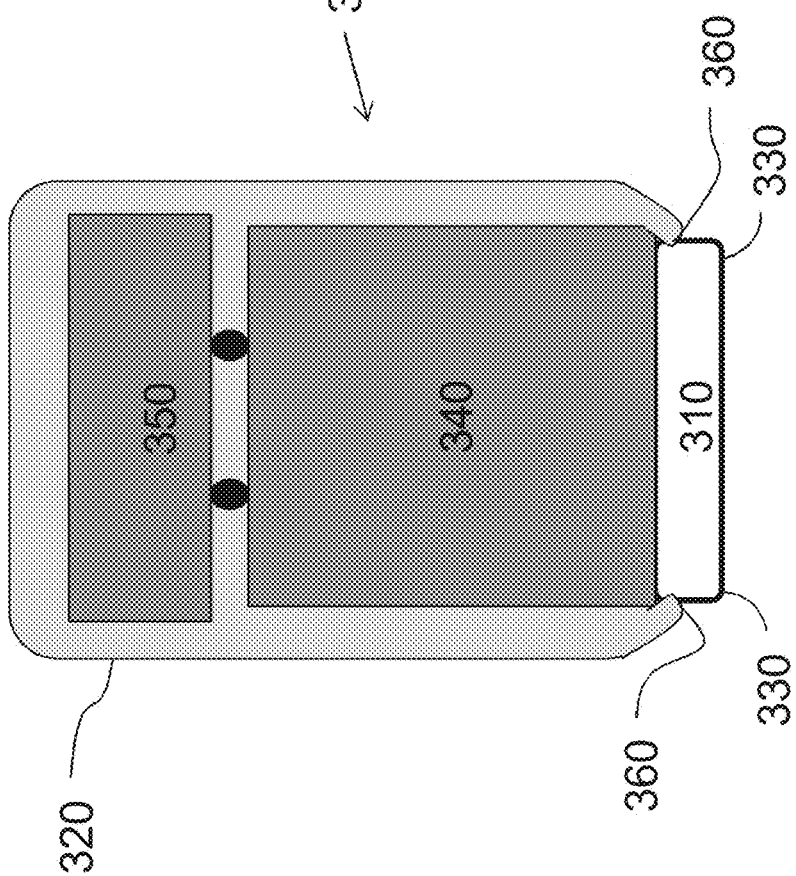
FIG. 3A shows an alternative depiction of an implant with two implant components mechanically connected to one another.

FIGS. 3A and 3B show an alternative embodiment of an implant 300 (leadless cardiac pacemaker) with a first implant part 310, which has tissue anchors 330 for anchoring to the myocardium and with a second implant part 320, which as an active implant part includes a battery 340 and electronic components 350. The locking between the first implant part 310 and the second implant part 320 is in this case provided by a detent connection 360, in which detent protrusions on the second implant part 320 engage in corresponding detent depressions on the first implant part 310.

If the battery 340 by way of example swells at the end of its life cycle or as a result of a targeted discharge following receipt of a corresponding telemetry signal, its swelling outer contour presses against an outer contour of the first implant component 310 disposed opposite. The locking by a detent connection between the first implant component 310 and the second implant component 320 is constructed here so that the swelling of the battery 340 causes the detent connection to release, so that the first implant part 310 and the second implant part 320 are then mechanically separated from one another.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The following is a summary list of reference numerals and the corresponding structure used in the above description of the invention:

| | |
|---|---|
| 100, 200, 300 | implant (cardiac pacemaker) |
| 110, 310, 310 | first implant part |
| 120, 220, 320 | second implant part |
| 130 | nitinol anchor |
| 140 | myocardial tissue |
| 150 | mechanical connection (locking device) |
| 230 | anchor |
| 240, 340 | electromechanical component (battery) |
| 250 | control/therapy electronics unit |
| 260 | locking lever |
| 270 | telemetry unit |
| 280 | stimulation unit |
| 290 | stimulation electrode |
| 350 | electronic component |
| 360 | detent connection |

The invention claimed is:

1. An active electrical implant or implant system, comprising:
    an energy supply unit;
    at least one fixation for permanently fixing the electrical implant or implant system to bodily tissue;
    at least two implant components releasably mechanically connected to one another, said at least two implant components including a first implant component having at least parts of said fixation and a second implant component having an electromechanical component being part of said energy supply unit, said electromechanical component having an outer contour, said electromechanical component swelling as a result of a current drain or a current feed to cause a swelling at said outer contour of said electromechanical component at least at one point; and
    said electromechanical component being disposed in such a way that said swelling of said electromechanical component results in a separation of said mechanical connection between said first and second implant components.

2. The active electrical implant or implant system according to claim 1, wherein said electromechanical component includes an electrical energy storage device.

3. The active electrical implant or implant system according to claim 2, wherein said electrical energy storage device includes at least one of a battery or a capacitor.

4. The active electrical implant or implant system according to claim 3, wherein said electromechanical component is a battery or includes a battery, and the active electrical implant or implant system is configured to deeply discharge said battery in order to trigger said swelling of said electromechanical component.

5. The active electrical implant or implant system according to claim 3, wherein said electromechanical component is a capacitor or includes a capacitor, and the active electrical implant or implant system is configured to discharge said capacitor beyond its nominal voltage in order to trigger said swelling of said electromechanical component.

6. The active electrical implant or implant system according to claim 3, wherein said electromechanical component is an electrolytic capacitor or includes an electrolytic capacitor, and the active electrical implant or implant system is configured to charge said electrolytic capacitor against its polarity in order to trigger said swelling of said electromechanical component.

7. The active electrical implant or implant system according to claim 1, wherein said electromechanical component is an encapsulated part causing said swelling when a voltage is applied or a current is injected, due to gas forming as a result of electrolysis in said encapsulated part.

8. The active electrical implant or implant system according to claim 1, which further comprises a telemetry unit triggering a swelling of said electromechanical component following receipt of a corresponding telemetry signal.

9. The active electrical implant or implant system according to claim 1, wherein said electromechanical component is part of said energy supply unit and includes a battery, and said electromechanical component is dimensioned to cause a separation of said mechanical connection between said first and second implant components when said battery of said energy supply unit is fully depleted.

10. The active electrical implant or implant system according to claim 9, wherein said battery of said energy supply unit is disposed and dimensioned to swell to such an extent that it causes a separation of said mechanical connection between said first and second implant components when said battery is fully depleted.

11. The active electrical implant or implant system according to claim 1, which further comprises a detent connection mechanically connecting said first and second implant components to one another, said outer contour of said electromechanical component swelling as a result of a current drain or a current feed bearing against an outer contour of said first implant component in a state in which said two implant components are latched to one another.

12. The active electrical implant or implant system according to claim 1, wherein the implant is an implantable cardiac pacemaker without electrode leads.

13. The active electrical implant or implant system according to claim 1, wherein the implant is an implantable sensor.

14. The active electrical implant or implant system according to claim 1, wherein the implant is a sensor lead or electrode lead.

\* \* \* \* \*